United States Patent [19]
Osborne

[11] Patent Number: 5,469,858
[45] Date of Patent: Nov. 28, 1995

[54] ECG P-QRS-T ONSET/OFFSET ANNOTATION METHOD AND APPARATUS

[75] Inventor: Jeffrey C. Osborne, McMinnville, Oreg.

[73] Assignee: Hewlett-Packard Corporation, Palo Alto, Calif.

[21] Appl. No.: 213,890

[22] Filed: Mar. 15, 1994

[51] Int. Cl.⁶ ............................................. A61B 5/0402
[52] U.S. Cl. ................................................... 128/710
[58] Field of Search ................................ 128/696, 710, 128/703, 704

[56]  References Cited

U.S. PATENT DOCUMENTS

| | | | |
|---|---|---|---|
| 4,509,530 | 4/1985 | Curtis et al. | 128/710 |
| 4,964,410 | 10/1990 | Leahey et al. | 128/710 |
| 5,224,486 | 7/1993 | Lerman et al. | 128/710 |

*Primary Examiner*—William E. Kamm
*Assistant Examiner*—Scott M. Getzow

[57] ABSTRACT

An annotation channel is added to an ECG printout to graphically display the temporal relationship between P, QRS, and T waves. The annotation channel displays similar waves from different ECG channels at vertically adjacent locations so an operator can quickly verify that ECG numerical data generated by the ECG system is derived from ECG signals with reasonably detected onset and offset reference locations. To further simplify wave correlation, a set of reference identifiers are generated along a vertical line at the beginning of the first wave. The reference identifiers provide individual reference points that graphically identify time shifts between the different starting points of each recorded wave.

21 Claims, 8 Drawing Sheets

ECG P-QRS-T ONSET/OFFSET ANNOTATION METHOD AND APPARATUS

BACKGROUND OF THE INVENTION

This invention relates generally to electrocardiogram (ECG) recording and display equipment and more particularly to a method for graphically annotating ECG data.

FIG. 1 is a graph showing the printout of three channels from an ECG. Each ECG signal from channels 1, 2, and 3 consists of a sequence of ECG cycles 11 each representing an individual heart beat. Each ECG cycle 11 may include three separate wave complexes defined as P, QRS, and T. Each wave complex defines a specific stage in the patient's heart beat. The three waves' complexes are shown bracketed within the first ECG cycle 11 of ECG channel 1.

The ECG signals in channels 1, 2, and 3 are derived from electrode readings. An "electrode" is an adhesive patch (or metal plate) that is placed on the patient's skin and connected to a wire coming from the cardiograph. For a routine 12-lead resting ECG, ten electrodes are required. An electrode is attached to each of the limbs (right/left arm/leg: RA, LA, RL, LL) and six electrodes are arrayed across the left chest at anatomically-determined positions (V1 through V6).

From the signals captured by the electrodes, two sets of ECG "leads" are generated. The "limb leads" are formed from the RA, LA, and LL electrodes as follows:

I=LA–RA

II=LL–RA

III=LL–LA aVR=RA–0.5*(LA+LL)

aVL=LA–0.5*(RA+LL)

aVF=LL–0.5*(LA+RA)

Similarly, the "chest leads" are formed by subtracting the average of RA+LA+LL from the corresponding chest electrode at each sample point. For example, lead V1= electrode V1–[(RA+LA+LL)/3].

The channels 1, 2, and 3 refer to a standard 3×4 presentation of ECG waveforms on the ECG report. Channel 1 contains 2.5 seconds of ECG leads I, aVR, V1, and V4. Similarly, channel 2 contains leads II, aVL, V2, and V5 and channel 3 contains leads III, aVF, V3, and V6. FIG. 1 shows the first 2.5 seconds of leads I, II and III. The additional leads are shown in their entirety in FIG. 5.

In a given heartbeat, the ECG signal read by each electrode is different. The electrodes are placed in different locations. ECG electrodes are "directional" in their ability to detect electrical heart activity. Each electrode records that portion of the net heart electrical activity that moves towards or away from that electrode's position. However, net electrical activity of the heart that moves perpendicular to the electrode's directional view is not recorded. Therefore, each electrode has a different perspective on heart activity. The directional variance in the different ECG electrodes creates differences in the magnitude, direction, and relative position of each ECG wave. Thus, electrodes placed in different locations on a patient, such as, on the limbs and chest, produce varied responses to the same heart beat.

Each P, QRS, and T wave has a specific beginning referred to as a wave onset and an end referred to as a wave offset. Because of the different perspectives of the electrodes, there is a built-in and normal variation from lead to lead of the onset and offset for each P, QRS, and T wave. In fact, in some leads in some ECGs, a P or QRS or T may not be "seen" at all when the net electrical activity in the heart takes place perpendicular to the electrode's viewpoint.

Additional variances in ECG readings are also caused by noise, for example, from body movements or from AC power interference. The amount of shift in the onset and offset of ECG waves also depends upon how the ECG system processes the noise. For example, there may be smaller shifts between recorded ECG signals if a detection algorithm is capable of detecting and subsequently rejecting noise.

In the presence of noise in the ECG and as a result of imperfect algorithms for determining true onsets and offsets, the variation in onsets/offsets between leads also contains a component that is due to "measurement error". Sometimes these are true errors when the measurement program becomes confused. More frequently these errors are better described as simple inaccuracies in determining the onset/offset times.

Typical ECG systems such as the Hewlett-Packard PageWriter XLi cardiograph, detect the P, QRS, and T waves and then produce numerical results. The measurements shown at 10 are only three of more than 800 numerical results, collectively known as the "measurement matrix", produced by the measurement program for an ECG. There are more numerical results in a "measurement table" from which the onsets and offsets for the annotation process are extracted. The numerical results such as 10 are derived according to the onset and offset of each P, QRS, and T wave. Therefore, if the onset or offset of a wave complex is inaccurate, the numerical data may also be inaccurate.

To verify that the numerical results 10 are correct, a physician examines the ECG signals in channels 1, 2, and 3. If any anomalous results appear in the individual ECG signals, there is a probability that the numerical results may be inaccurate. Thus, the physician is either notified that the numerical data is potentially wrong or is reassured that the numerical data is reliable. The physician examining the ECG signals, however, typically does not know where the ECG system designates the specific onset and offset locations for each P, QRS, and T wave. Therefore, it is difficult to accurately assess whether the ECG signals detected by the measurement program in channels 1, 2, and 3 are accurately aligned or are erroneously offset to such a degree where the validity of the numerical data 10 is in question. Thus, there is no quick and accurate way shown in FIG. 1 to correlate the measurement program's decisions regarding onsets and offsets of wave complex components to verify numerical ECG data.

One method for verifying the numerical ECG data 10 is shown in FIG. 2. Referring to FIG. 2, tick marks are superimposed at the onset and offset of each P, QRS, and T wave. For example, a tick mark 12 and a tick mark 14 are superimposed at the derived onset and offset points, respectively, on the first P-wave of the ECG signal in lead I. Correspondingly, a tick mark 16 and a tick mark 18 are superimposed at the derived onset and offset points, respectively, on the first P wave of the ECG signal in lead II and tick marks 20 and 22 are superimposed on the first P wave of the ECG signal in lead III.

Each tick mark defines either the beginning or end of the associated P wave. Thus, an ECG system operator can verify that the wave onset and wave offset for one particular wave complex are aligned with the onset and offset for the same wave complex in the two adjacent channels. For example, the ECG system operator looks at the relative horizontal positions of tick marks 12, 16, and 20. If each tick mark is substantially aligned in a vertical column, it is likely that each P wave was accurately measured and detected at approximately the same time. It is then more likely that the numerical data 10 is based on accurate ECG measurements. The onset and offsets of the QRS wave and the T wave in ECG lead I are similarly identified with tick marks.

Superimposing tick marks on the ECG signals as shown in FIG. 2, however, has two distinct disadvantages. The first disadvantage is that the tick marks are obstructive to the ECG waveform data at the onset and offset locations. Specifically, the tick marks hide the ECG signal and disrupt normal view of each channel. The second disadvantage is that it is difficult to correlate the onset and offset locations for the same wave complexes on different ECG channels. For example, slight shifts in time between different waveforms is difficult to discern because of the spacial displacement between adjacent waveforms. Specifically, there is too much distance between tick marks 12, 16 and 20 to accurately determine the amount of relative shift between the derived onset of each P wave.

Accordingly, a need remains for displaying ECG data so that information between associated ECG signals can be quickly and accurately correlated.

SUMMARY OF THE INVENTION

It is, therefore, an object of the invention to detect variations in the derived onsets and offsets of P, QRS, and T waves in ECG data.

Another object of the invention is to graphically correlate the decisions regarding the labeling and determination of the onset and offset of various parts of the ECG signals.

A further object of the invention is to graphically identify individual waveform information contained in ECG signals.

An annotation channel is added to an ECG printout to graphically display the temporal relationship between the onsets and offsets of multiple P, QRS, and T waves. The annotation channel displays similar waves from different ECG channels at vertically adjacent locations so that the time shifts between each wave can be quickly and accurately correlated. Each wave in the annotation channel is represented by an array of horizontally aligned dots that begin at the onset of the wave and end at the wave offset.

A second horizontal line representing the same wave from a second channel is displayed in a similar manner directly below the first horizontal line. [A third line representing a third channel is similarly displayed below the second horizontal line.] Therefore, the temporal relationship between the two waves can be easily discerned from the alignment of the two horizontal lines.

A set of horizontal lines are generated for each set of P, QRS, or T waves and are displayed at the same relative times that the wave actually occurs on the ECG signal. The annotation channel can then be quickly scanned to verify that ECG numerical data generated by the ECG system is derived from ECG signals with reasonably detected onset and offset reference locations. To simplify wave detection and correlation, a set of dots are generated along a vertical line at the location where the wave first begins. The vertical line is used to identify and provide individual reference points for the beginning of each P, QRS, and T wave.

Since the length of each horizontal line is proportional to the duration of the associated ECG wave, it is easy to correlate the offset of each corresponding wave. For example, if a first P wave ends before two corresponding P waves, the horizontal line associated with the first P wave will terminate before the horizontal lines associated with the second and third P waves.

The annotation channel can be displayed for any ECG display configuration and utilizes existing measurement tables generated by the ECG system. The measurement table contains onset and offset information for each P, QRS, and T wave. A second copy of the annotation channel is optionally generated so that annotation channels can be located both above and below the ECG waveforms. Two annotation channels eliminate parallax errors in correlating annotation channel information with ECG waveforms.

Alternatively, the horizontal lines associated with each P, QRS, or T wave can simply be used as a digital representation of the analog ECG signals displayed on the individual display channels. The digital wave representations in the annotation channel provides detection, position, duration, and labeling information for each ECG wave while removing other data and noise. Thus, critical patient information can be extracted more quickly and more accurately a present ECG display formats.

The foregoing and other objects, features and advantages of the invention will become more readily apparent from the following detailed description of a preferred embodiment of the invention which proceeds with reference to the accompanying drawings.

DETAILED DESCRIPTION

Figure 3:
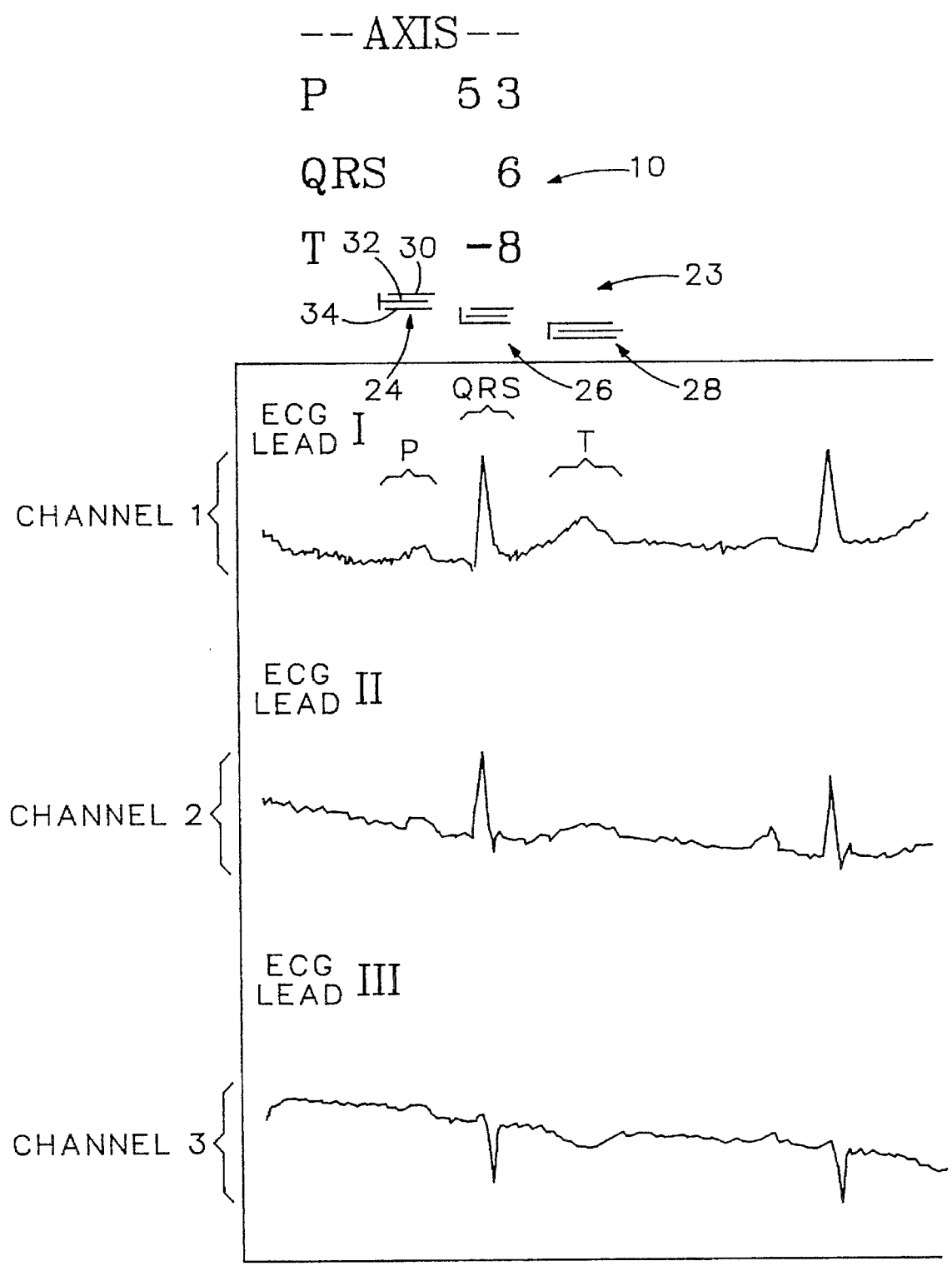
FIG. 3 is a graph showing an ECG printout including an annotation channel according to the invention.

FIG. 3 is a graph showing an ECG printout from an ECG system according to a first embodiment of the invention. Above the three ECG channels 1, 2, and 3 is an annotation channel 23 that includes three graphics 24, 26, and 28. Graphic 24 represents a set of annotated P waves from ECG signals in channels 1, 2, and 3, graphic 26 represents a set of annotated QRS waves from the ECG signals in the three channels and graphic 28 represents a set of annotated T waves from the ECG signals in the three channels.

Referring to graphic 24, horizontal line 30 represents the P wave from the ECG signal in channel 1. Horizontal lines 32 and 34 represent the P waves from the ECG signals in channels 2 and 3, respectively. Each horizontal line in each graphic 24, 26, and 28 is positioned directly over the corresponding wave. For example, horizontal line 32 begins at the same time as the onset of the first P wave from channel 2. Horizontal line 32 ends at the same time as the corresponding offset of the first P wave from channel 2.

The graphics are derived from the same data base used to determine numerical data 10. Thus, each horizontal line substantiates that the corresponding wave has been acknowledged in the measurements used to derive ECG measurements. For example, if any of the three horizontal lines in any one graphic in annotation channel 23 are missing, the ECG system did not detect the associated ECG wave.

Figure 4:
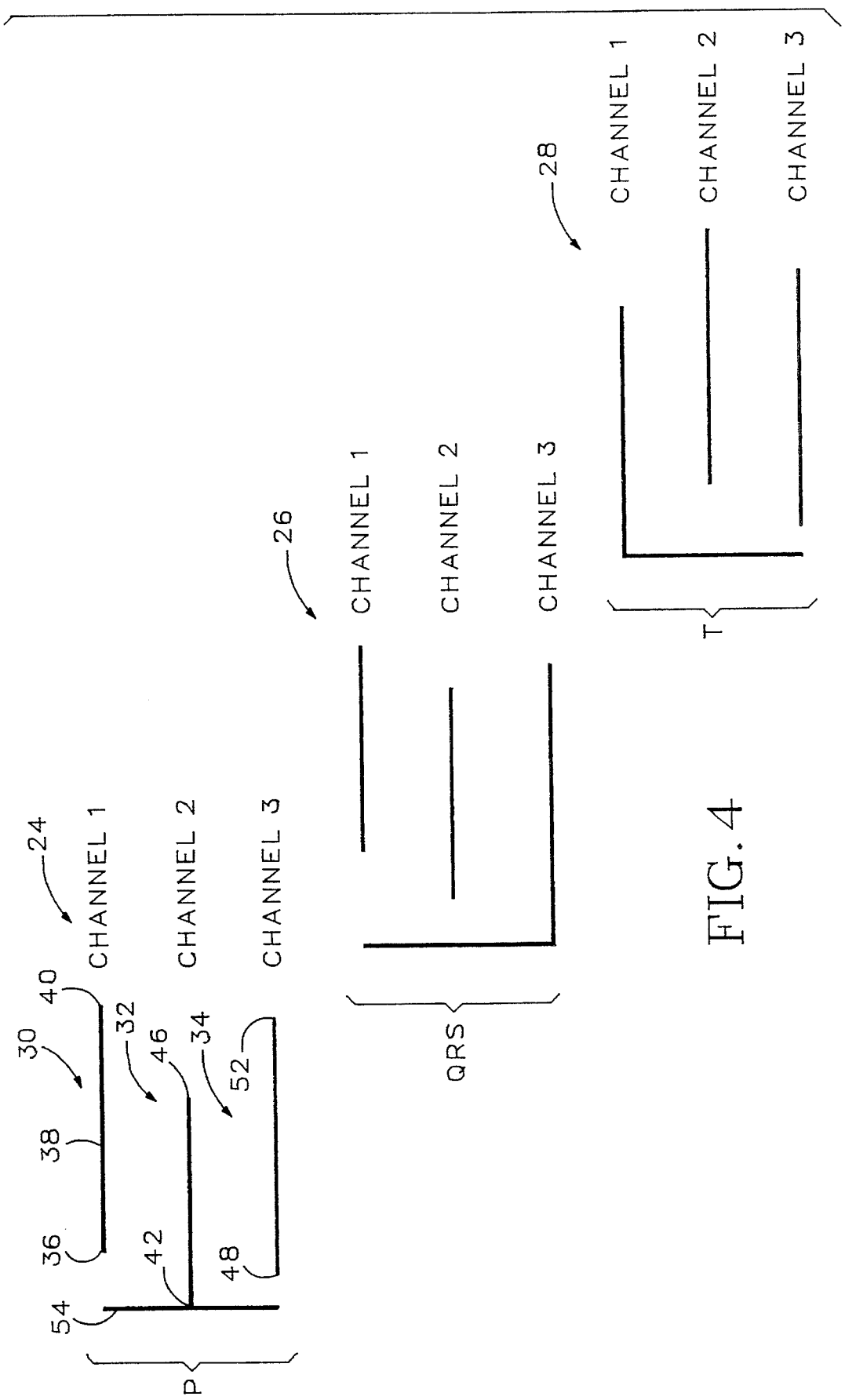
FIG. 4 is a detailed graph showing individual graphics from the annotation channel in FIG. 3.

FIG. 4 is a graph showing in more detail the individual graphics 24, 26, and 28 from annotation channel 23 in FIG. 3. In addition to verifying that the associated wave was actually identified by the ECG system, each graphic 24, 26, and 28 also annotates the derived onsets and offsets of wave detection. For example, each horizontal line provides information about wave onset, offset, duration and relative location with respect to the waves from the other two channels.

Figure 1:
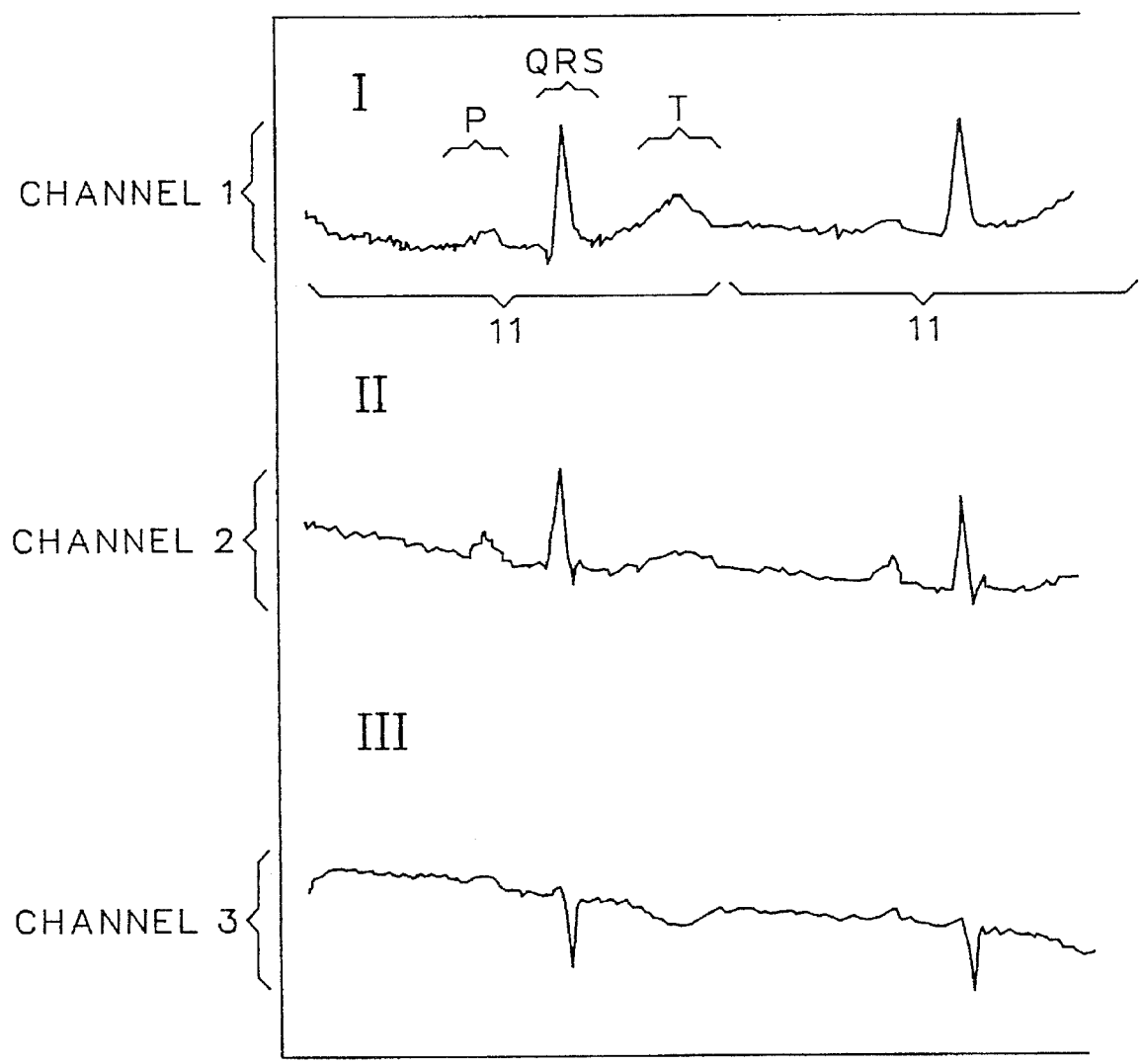
FIG. 1 is a prior art graph showing three channels of ECG data.
Figure 2:
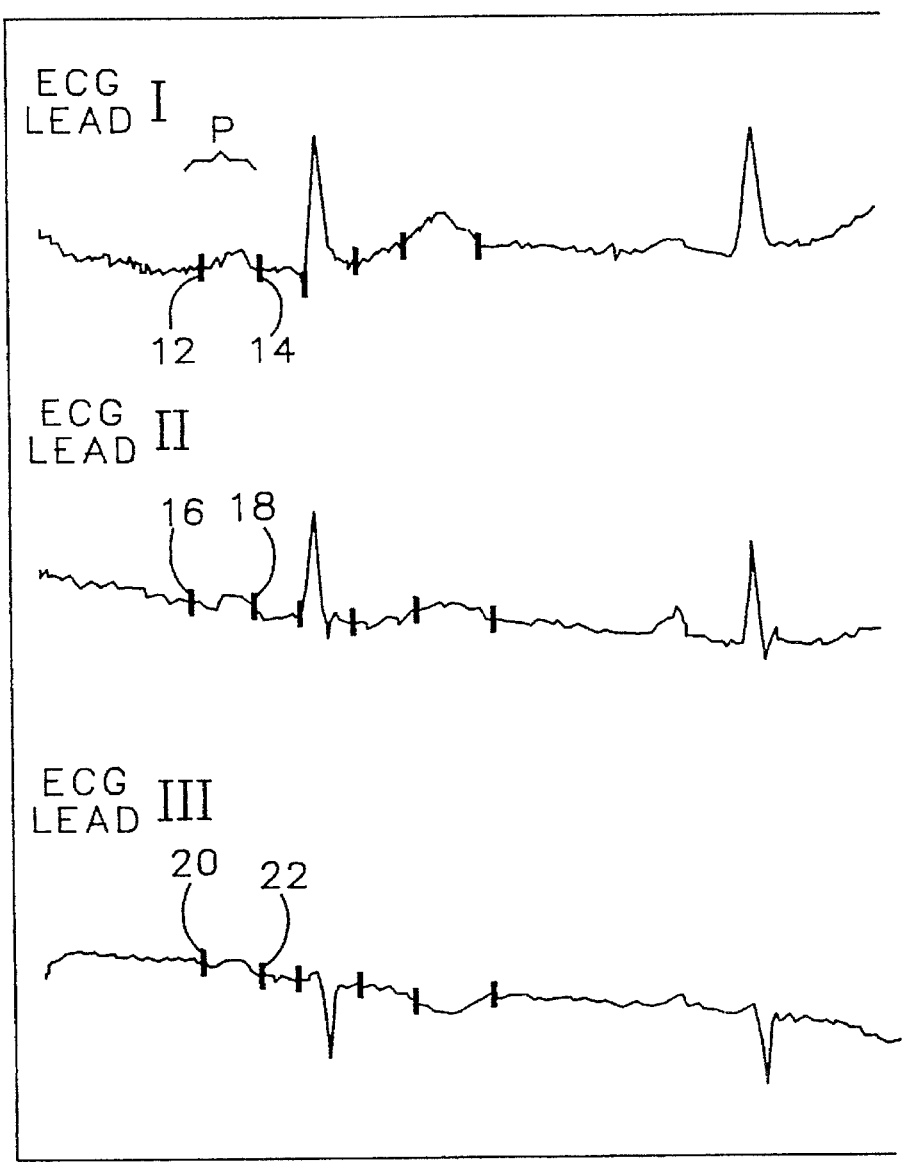
FIG. 2 is the graph of FIG. 1 with tick marks superimposed at the onset and offset of each P, QRS, and T wave.

Referring to graphic 24, horizontal line 30 represents the first P wave from the ECG signal in channel 1 (FIG.3). The beginning of horizontal line 30 at point 36 corresponds to the onset of the P wave and the end of line 30 at point 40 corresponds to the offset of the P wave. To further accentuate the detection of the P wave, a sequence of horizontal dots 38 connect points 36 and 40. The annotation channel also identifies the type of wave whose onset and offset is being displayed based on where in the annotation channel the horizontal line is drawn. With tick marks there is no way of knowing whether the program considered a particular wave to be a P, QRS, or T wave. Thus, the graphic is more descriptive of the associated ECG wave than the individual tick marks shown in FIG. 2.

Each dot that makes up line 30 represents a discrete time instance during the P wave. Based on the existing wave detection process performed by the ECG system, that is discussed further below, a graphic display process enables a graphic indicator (e.g., dot) at each location along a horizontal path that resides between the onset and offset of the P wave, thereby creating line 30. Lines 32 and 34 are created in a similar manner for the first P waves in the ECG signals in channels 2 and 3, respectively.

A series of vertically aligned dots establish line 54 at the horizontal location that defines the first onset for any one of the three P waves. For example, in graphic 24, the P wave in channel 2 occurs before the onset of the P waves in channels 1 and 3. Therefore, vertical line 54 is established at the starting point 42 of line 32. Graphics 26 and 28 provide the same graphic correlation, however, in graphic 26 the onset for the QRS wave in channel 3 occurs before the QRS waves in channels 1 and 2. Therefore, the vertical line begins at the starting point of the channel 3 horizontal line.

The vertical line is most useful when a given P, QRS or T wave is detected in only one or two channels. In the case of single channel detection, without the vertical line only a single horizontal line would be seen. It would be very difficult to tell whether that line represented a wave in channel 1 or 2 or 3. By drawing a vertical line at the earliest onset it becomes obvious which channel is represented. If the horizontal line is at the top of the vertical line, channel 1 data is represented, in the middle channel 2, and if a horizontal line is attached at the bottom of the vertical line, channel 3.

Vertical line 54 also allows timing information to be easily gleaned from the relative positioning for each P wave. For example, vertical line 54 extends up to the same vertical location as line 30 and down to the same vertical location as line 34. Therefore, the horizontal distance between vertical line 54 and the starting point 36 gives an easy to correlate visual indication of the time delay between the onset from the P wave in channel II and the onset from the P wave in channel 1.

The distance between vertical line 54 and point 48 indicates the time delay between the onset from the P wave in channel 2 and the onset from the P wave in channel 3. Thus, as the distance widens between any of the three starting points 36, 42, or 48 and vertical line 54, there is a greater relative shift between the derived onset of each P wave. The P wave end points 40, 46 and 52 provide a graphical correlation between the time of each P wave offset. For example, end point 46 from the P wave in channel 2 occurs before the end points 40 and 52.

Figure 5:
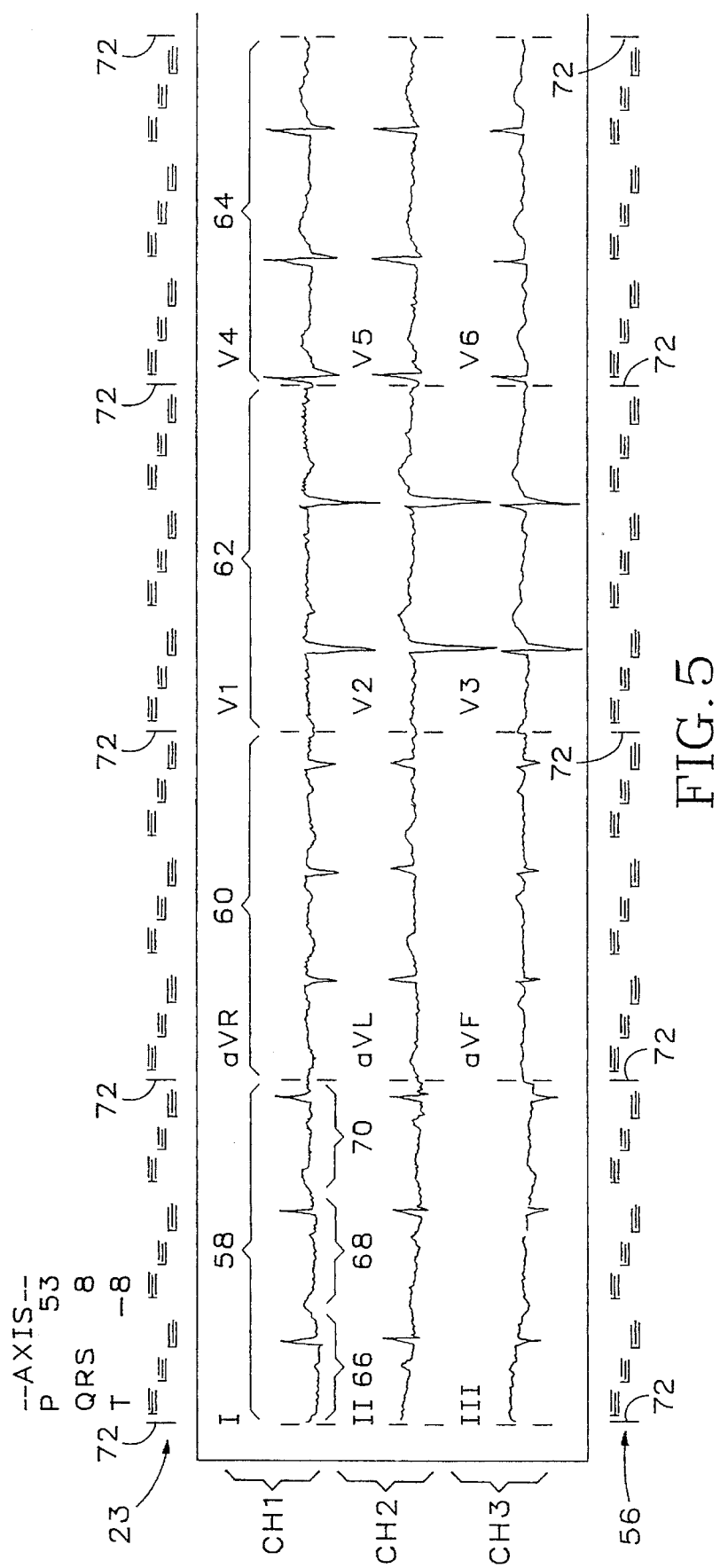
FIG. 5 is a graph showing an ECG printout with two annotation channels.

FIG. 5 is an ECG printout with two annotation channels 23 and 56. Annotation channel 56 is located below ECG channels 1, 2, and 3 to provide a second reference for identifying which set of P, QRS, or T waves are associated with each graphic. The graphics in annotation channel 56 are identical to the graphics in annotation channel 23. It is important to note that the annotation channels can be derived for any ECG output configuration.

For example, FIG. 5 shows a 3×4 printout having 3 channels (1, 2, 3) of ECG data each separated into 4 columns or leadsets 58, 60, 62, and 64. Each leadset represents a different set of ECG signals obtained from unique electrode combinations. Each leadset displays an ECG signal for approximately 2.5 seconds. Alternatively, the ECG printout is arranged into six channels each having two leadsets each displaying approximately 5.0 seconds of ECG data.

Each leadset displays electrical impulses in three different channels. Therefore, a total of twelve separate ECG signals are displayed in FIG. 5. Each leadset can display multiple heartbeat cycles as shown by heartbeat cycles 66, 68, and 70. A graphic is generated for each detected P, QRS, and T wave in each heartbeat cycle in each leadset. The "line," 72, is made up of dots representing the unoccupied dot rows in the 16-dot high annotation channel. The lines, 72, also appear in the annotation channel, 56. Additional vertical lines 72 are drawn in the annotation channel to identify the beginning and end of each leadset. The annotation channel is output from any ECG system used to print the ECG data. Alternatively, the annotation channel can be displayed on a CRT or any alternative display medium.

Figure 6:
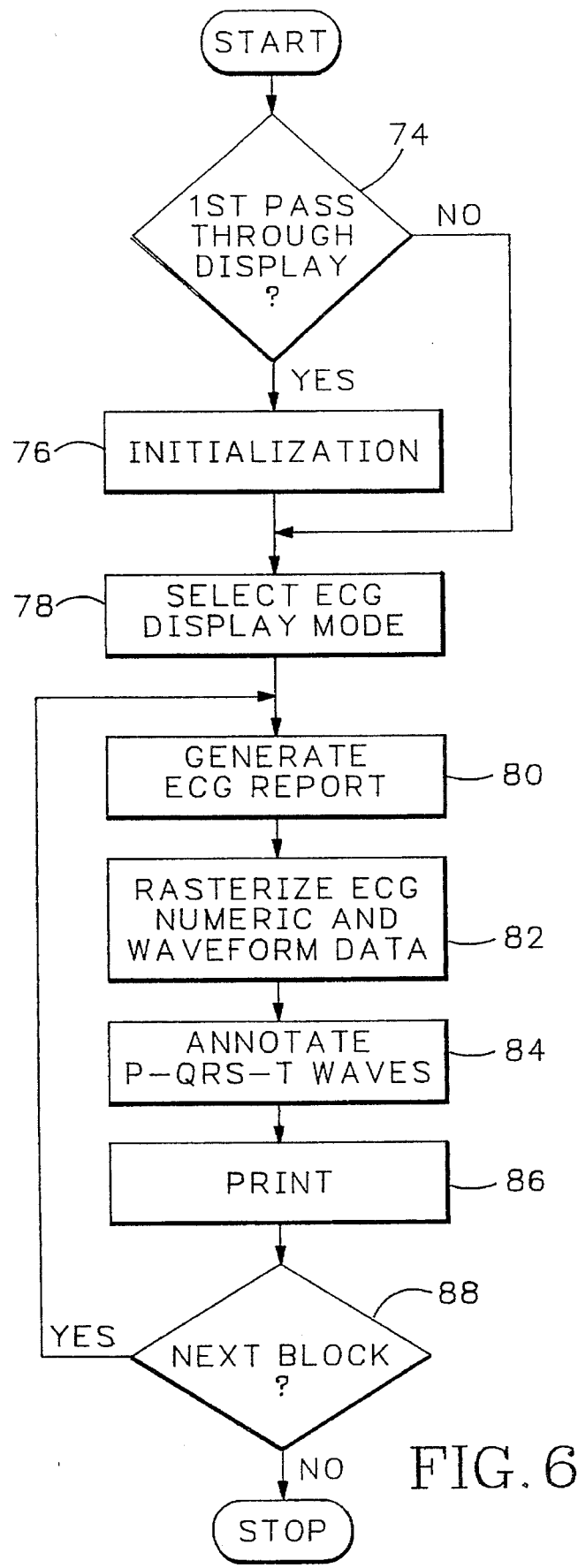
FIG. 6 is a flow diagram showing the method for printing ECG data.

FIG. 6 is a flow chart showing a method for generating the ECG printout shown in FIG. 5. Most of the blocks in FIG. 6, except for block 84, are commonly performed print procedures known to those skilled in the art and, therefore, are not described in detail. The annotation process performed in block 84, however, is described in detail in FIG. 7.

Referring to FIG. 6, decision block 74 determines if it is the first time through the ECG print process. A first pass through the ECG print process requires that block 76 initialize variables for the ECG print process. If the printing initialization parameters have already been initialized, decision block 74 jumps to block 78 where the desired ECG display mode is selected. As explained above in FIG. 5, various ECG waveform formats are selectable for the ECG printout. For example, a 6×2 format displays six horizontal channels of data each separated into two leadsets of approximately 5.0 seconds. Alternatively, the ECG waveforms can be displayed in three horizontal channels each channel separated into four leadsets of 2.5 seconds as shown in FIG. 5. Additional formats are also possible.

After the print format is selected, block 80 gathers a given amount of data from a patient and then in a batch process measures and interprets the ECG data and generates a report. The ECG report contains all information about each P, QRS, and T wave used to generate numerical data 10 (FIG. 3).

Block 82 then rasterizes all character data and ECG waveform channels. Block 84 annotates the P,QRS, and T waves from each ECG channel according to onset and offset information previously derived in the ECG report generated in block 80. There are various amplitudinal and temporal methods for determining the onset and offset of P,QRS, and T waves. Any of these methods can be utilized to provide the onset and offset information utilized in block 84. Algorithms for detecting the onset and offset of ECG waves are known to those skilled in the art and are therefore not explained in detail.

Block 84 annotates the P, QRS, and T waves displayed in channels 1, 2, and 3 as the annotation channel 23 previously shown in FIG. 3. In one embodiment, the annotation channel is 16 dots wide and extends the entire length of the ECG printout. Block 86 then prints the ECG character data, waveform data and the annotated P, QRS, and T information. If there is more ECG data that needs to be processed for the printout, decision block 88 jumps back to block 80 where the next set of dot columns are processed, rasterized and printed. After all ECG data has been processed and printed, the print process shown in FIG. 6 stops.

Figure 7A:
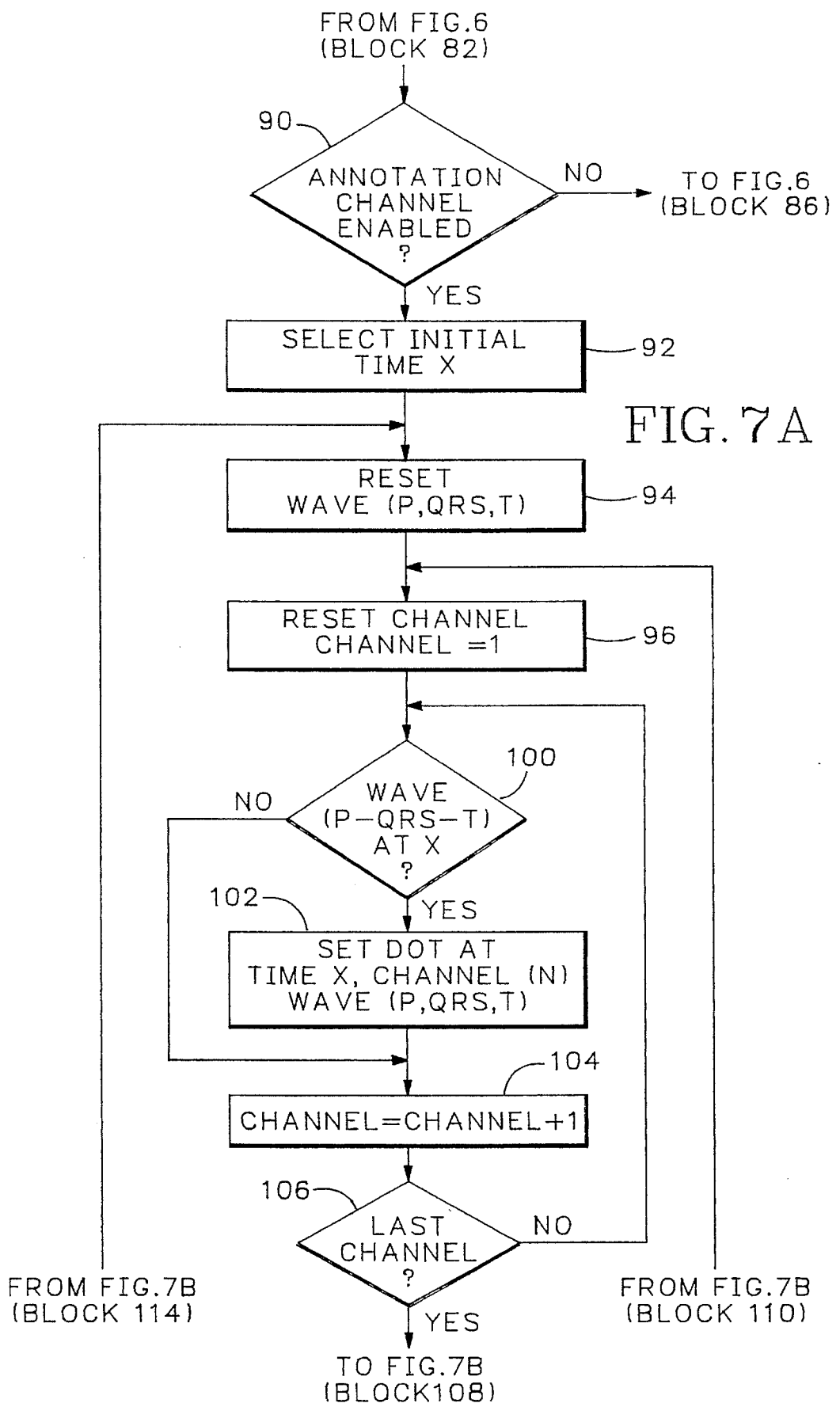
FIGS. 7A and 7B are a detailed diagram showing the method for generating the annotation channel shown in FIG. 3.
Figure 7B:
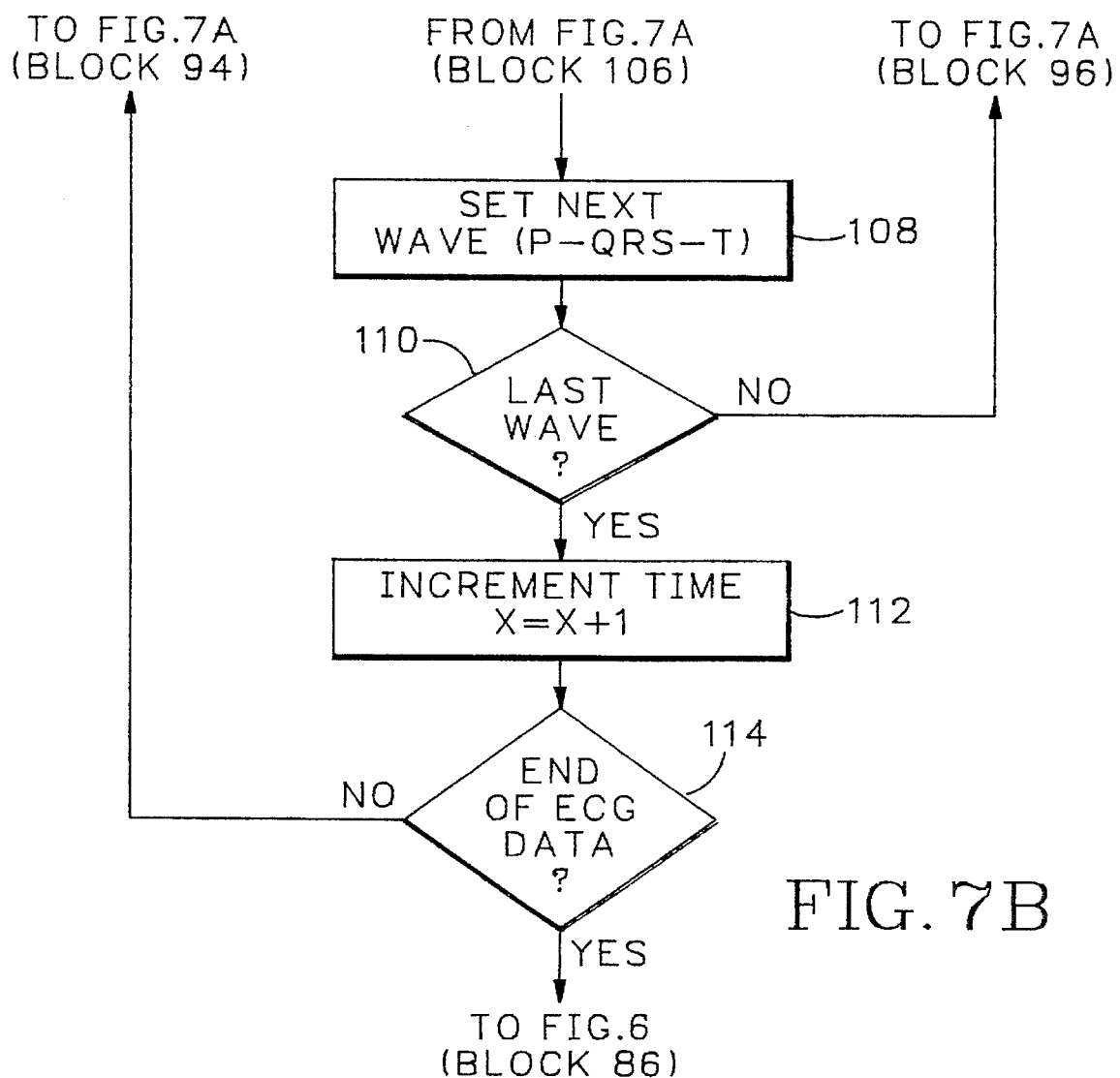

FIGS. 7A and 7B are a detailed flow diagram of the annotated P-QRS-T block 84 in FIG. 6. In the ECG system described above, the printing routine is performed by buffering and then printing data in two-character wide blocks of dot columns. Each two-character wide block represents a block of time during the ECG waveform. Two-character blocks of rasterized data are output repeatedly until an entire page of ECG data is output. Each two-character block contains multiple dot columns that represent specific instances of time. The dot columns within the annotation channel are set or unset according to the P, QRS, or T data in the ECG channels at the same relative time instances. Slicing an ECG printout into a series of character columns is a standard process known to those skilled in the art and is, therefore, not described in detail.

Each character column contains approximately 20 dot columns, therefore, approximately 40 distinct instances of time must be processed for each buffered block of rasterized data. As described in FIG. 6. by the time the process is ready to annotate P, QRS, and T waves, the ECG system has already measured the ECG data, determined the onset and offset of each P, QRS, and T wave, and has rasterized the ECG character and waveform data. The annotated P-QRS-T block 84 (FIG. 6) then utilizes the ECG measurements previously derived from the ECG system to generate the annotation channel.

It is important to note that the graphics displayed in the annotation channel correspond with the actual algorithms used to generate ECG numerical data. For example, it is important to use the same onset and offset values used by the ECG system to generate the numerical data 10 (FIG. 3). This ensures that the graphics in annotation channel 23 correspond exactly with the onset and offset values used for ECG calculations.

Referring to FIG. 7A, decision block 90 determines whether the annotation channel has been enabled. If the annotation has not been enabled, decision block 90 jumps to block 86 (FIG. 6) where the ECG print process is performed without generating an annotation channel. If the annotation channel has been enabled, block 92 selects a first dot column for processing. The dot column along with the leadset number Y (see FIG. 5) are converted into an instance in time X that is used as a reference for accessing the ECG table generated in block 80 (FIG. 6).

Block 94 resets a variable WAVE to begin searching the ECG table for a P wave and block 96 sets a variable CHANNEL to one. Decision block 100 searches the ECG table in leadset Y to determine whether the time X occurs between the onset and offset of the P wave in the first channel. If time X does occur during the first P wave in channel 1, block 102 sets a graphic indicator (dot) in the associated dot column in line 38 (FIG. 4). If time X does not occur between the onset and offset of the P wave from channel 1, no dot is set in the associated dot column and decision block 100 jumps to block 104 where the variable CHANNEL is incremented to channel 2.

If the previously searched P wave is not the last channel in the leadset (i.e., channel 3), decision block 106 jumps back to decision block 100 where it is determined whether time X occurs between the onset and offset of the first P wave from channel 2. In a similar manner, if the P wave from channel 2 occurs during time X, the associated dot column is set in line 32 (FIG. 4).

After the P wave in channel 3 is searched, decision block 106 jumps to block 108 where the WAVE variable is set to search the next wave type. For example, block 108 resets WAVE to look for QRS waves. Decision block 110 checks to see if all P, QRS, and T waves have been searched. If each wave type has not been searched, decision block 110 jumps back to block 96 where the variable CHANNEL is reset back to one. The process then cycles through the process checking whether time X occurs between the onset and offset for each wave in each channel.

After each set of P, QRS, and T waves have been searched for each channel, decision block 110 jumps to block 112 where the time X is incremented. Time X is incremented by selecting the next adjacent dot column and then based on the dot column location and the leadset number deriving a time value. If the end of the ECG data has not been reached, decision block 114 jumps to block 94 where the variable WAVE is reset to point back to the P wave. The process then repeats the above described process, checking each P, QRS, and T wave in each channel and enabling the corresponding dot column in the graphic.

After all rasterized data has been annotated, decision block 114 jumps to block 86 (FIG. 6) where all data including the graphics from the annotation channel are printed. Thus, the process described above generates an annotation channel that graphically correlates the temporal relationship between the P, QRS, and T waves for multiple channels. The annotation channel increases the user's confidence in ECG measurement programs by giving the ECG user a way to see what reference points are used by the ECG measurement program to derive numerical data.

Again, from the description provided above, the software for generating the annotation channel would be easily implemented on an ECG system by one with average skill in the art.

Having described and illustrated the principles of the invention in a preferred embodiment thereof, it should be apparent that the invention can be modified in arrangement and detail without departing from such principles. I claim all modifications and variations coming within the spirit and scope of the following claims.

I claim:

1. A method for displaying a temporal relationship between various waves in an electrocardiogram, comprising:

detecting a beginning of a first wave from a first ECG channel;

detecting a beginning of a second wave from a second

ECG channel;

generating a first graphic identifier corresponding to the beginning of the first wave;

generating a second graphic identifier corresponding to the beginning of the second wave; and displaying the first and second graphic identifiers in a third channel and spacing the graphic identifiers at relative distances from each other proportional to the amount of time that has passed between the beginning of the first and second waves.

2. A method according to claim 1 including:

detecting the end of the first and second waves;

generating end graphic identifiers that correspond to the end of the first and second waves; and displaying the end graphic identifiers in the third channel at relative distances from each other proportional to the time difference between the ending of the first and second waves.

3. A method according to claim 1 wherein the first and second waves are both either P, QRS, or T waves.

4. A method according to claim 1 wherein the first and second graphic identifiers are displayed at a horizontal distance from each other, the horizontal distance proportional to the time delay between the beginning of the first and second waves.

5. A method according to claim 1 including displaying first and second horizontal lines associated with the first and second waves, respectively, each horizontal line starting at the beginning of the associated wave and ending at the end of the associated wave.

6. A method according to claim 5 wherein the second line is positioned underneath the first line and horizontally offset according to the time delay between the beginning of the first and second waves.

7. A method according to claim 1 further comprising displaying multiple P, QRS, T complex wave sequences in the first and second ECG channels, the beginning of each P, QRS, and T complex wave from each sequence in the first ECG channel being graphically compared with a corresponding complex wave from the second ECG channel.

8. A method according to claim 1 wherein the first and second graphic identifiers are displayed in the third channel at the same time that the beginning of the corresponding first and second waves are displayed.

9. A method according to claim 1 wherein the first and second waves are derived from electrodes located at different locations on a patient and the distance between the first and second graphic identifiers indicate measurement differences between the electrodes.

10. A method for graphically displaying electrocardiogram (ECG) waveform information, comprising:

generating an analog ECG signal derived from electrical impulses generated from the patient's heart;

detecting the beginning of a first wave in the ECG signal;

detecting the end of the first wave in the ECG signal; and displaying a digital graphic including a set of identifiers corresponding to individual instances of time occurring between the detected beginning and detected end of the first wave, the number of displayed identifiers proportional to the time duration of the wave.

11. A method according to claim 10 including:

generating multiple ECG waves corresponding to various heart conditions detected at different locations on the patient;

detecting the beginning and end of each ECG wave; and displaying a set of identifiers for each ECG wave in a manner similar to that displayed for the first wave.

12. A method according to claim 10 wherein the set of identifiers comprises a first set of identifiers, said first set being aligned with a second set of identifiers generated from a second wave generated from a second location on the patient, the first and second set of identifiers aligned according to the beginning of the first and second waves respectively.

13. A method according to claim 12 including generating a set of reference identifiers for providing a spatial reference for the first and second set of identifiers, the distance of each set of identifiers from the reference identifiers being proportional to the time difference between the beginning of the first and second wave.

14. A method according to claim 12 including generating a set of reference identifiers that indicate the existence of both the first and second sets of identifiers whereby location of the first and second sets of identifiers in relation to the set of reference identifiers indicates which waves have been detected.

15. A method according to claim 10 wherein the set of identifiers are aligned adjacent to each other in a horizontal row, a first identifier indicating the beginning of the first wave and a last identifier indicating the end of the first wave.

16. A method according to claim 10 including displaying the ECG signal in conjunction with the set of identifiers so that each identifier aligns with a corresponding location on the first wave.

17. A method according to claim 10 wherein the ECG signal contains P, QRS, and T complex waves and identifier sets are displayed for each complex wave.

18. A method for comparing electrocardiogram (ECG) signals detected from various locations on a patient, comprising:

capturing separate ECG signals from different locations on the patient;

generating multiple ECG waveforms, each ECG waveform corresponding to at least one of the captured ECG signals;

simultaneously displaying the ECG waveforms at the same relative instances in time in separate channels on a display;

detecting at least one set of complex waves that is common to each of the ECG waveforms;

generating graphic identifiers for corresponding ones of the complex waves within the one set, each graphic identifier corresponding to a selected point in time during the corresponding complex wave; and displaying the graphic identifiers in a first annotation channel for graphically correlating relative temporal differences between occurrence of the complex waves within the one set.

19. A method according to claim 18 wherein each graphic identifier comprises a string of horizontal identifiers that extend from beginning to end of the corresponding complex wave, each horizontal identifier representing a specific predetermined instance of time.

20. A method according to claim 18 including displaying a second annotation channel, the first and second annotation channels located above and below the ECG signal channels.

21. An ECG system comprising:

means for capturing separate ECG signals from different locations on a patient;

means for generating multiple ECG waveforms, each ECG waveform corresponding to at least one of the captured ECG signals;

means for simultaneously displaying the ECG waveforms at the same relative instances in time in separate channels on a display;

means for detecting at least one set of complex waves that is common to each of the ECG waveforms;

means for generating graphic identifiers for corresponding ones of the complex waves within the one set, each graphic identifier corresponding to a selected point in time during the corresponding complex waves; and means for displaying the graphic identifiers in a first annotation channel to graphically correlative relative temporal differences between occurrences of the complex waves within the one set.

* * * * *